United States Patent [19]

Pastor

[11] Patent Number: 5,145,970

[45] Date of Patent: Sep. 8, 1992

[54] STABILIZERS DERIVED FROM 3,5-DIALKYL-4-AMINOBENZENETHIOL

[75] Inventor: Stephen D. Pastor, Danbury, Conn.

[73] Assignee: Ciba-Geigy Corporation, Ardsley, N.Y.

[21] Appl. No.: 602,968

[22] Filed: Oct. 24, 1990

[51] Int. Cl.$^5$ ................. C07D 207/40; C07C 219/28; C07C 219/32

[52] U.S. Cl. ........................ 548/546; 560/17

[58] Field of Search ........................... 548/546; 560/17

[56] References Cited

U.S. PATENT DOCUMENTS 3,156,720  11/1964  Goldberg et al. .................... 252/97
3,224,972  12/1965  Orloff et al. ........................... 252/47
3,934,972   1/1976  Greenhalgh et al. ..................... 8/39
3,953,162   4/1976  Greenhalgh et al. ..................... 8/39

OTHER PUBLICATIONS

Chem. Abst. 60, 10600d.

Primary Examiner—David B. Springer
Attorney, Agent, or Firm—Luther A. R. Hall

[57] ABSTRACT

Compounds prepared by the addition of the mercaptan group of 3,5-dialkyl-4-aminobenzenethiol to activated ethylenic double bonds or the sulfenyl chloride of 3,5-dialkyl-4-aminobenzenethiol to trialkyl phosphites are effective stabilizers for organic material subject to oxidative and/or thermal degradation.

15 Claims, No Drawings

STABILIZERS DERIVED FROM 3,5-DIALKYL-4-AMINOBENZENETHIOL

The instant invention pertains to compounds containing at least one 3,5-dialkyl-4-aminophenylthio moiety which are effective stabilizers for organic materials subject to oxidative and/or thermal degradation.

BACKGROUND OF THE INVENTION

U.S. Pat. Nos. 3,156,720 and 3,224,972 disclose as antioxidants 4,4'-thiobis(2,6-dialkylanilines). These patents describe several 3,5-dialkyl-4-aminobenzenethiols, but not any of the instant compounds derived therefrom.

U.S. Pat. Nos. 3,934,972 and 3,953,162 mention unsubstituted 4-aminophenylthiosuccinic acid as a dye fixation agent. There is no mention of corresponding dialkyl or diaralkyl substituted compounds nor of the use of the unsubstituted succinic acids as stabilizers.

Belgian Patent No. 625,216 (=Chem. Abst. 60, 10600) discloses unsubstituted S-(4-aminophenyl)thiophosphorus acid esters as parasiticides. Again no mention of an stabilization efficacy for such esters is made.

OBJECTS OF THE INVENTION

One object of the invention is to provide new compounds containing at least one 3,5-dialkyl or diaralkyl-4-aminophenylthio moiety which are effective stabilizers for organic materials subject to oxidative and/or thermal degradation.

Another object of the invention is to provide stabilized compositions containing an organic material subject to oxidative and/or thermal degradation and an effective stabilizing amount of an instant compound described above.

Still another object of the invention is to provide for new mercaptan intermediates, such as 4-amino-3-tert-butyl-5-methylbenzenethiol, useful in preparing the stabilizer compounds of this invention.

DETAILED DISCLOSURE

The instant invention pertains to a compound of formula I

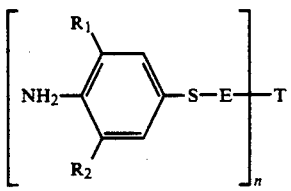

wherein
R$_1$ and R$_2$ are independently alkyl of 1 to 18 carbon atoms, cycloalkyl of 5 to 12 carbon atoms, phenylalkyl of 7 to 9 carbon atoms or said phenylalkyl substituted on the phenyl ring by alkyl of 1 to 4 carbon atoms,
n is an integer from 1 to 4,
when n is 1, E is a direct bond, and T is a group of formula II, III, IV, V or VI

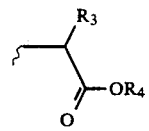

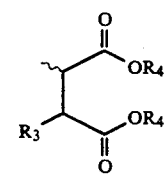

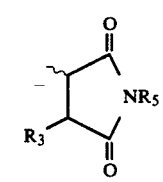

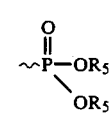

or

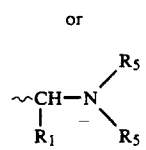

where
R$_3$ is hydrogen or methyl,
R$_4$ is alkyl of 1 to 30 carbon atoms, cycloalkyl of 5 to 12 carbon atoms, phenylalkyl of 7 to 9 carbon atoms, phenyl or said phenylalkyl or said phenyl substituted on the phenyl ring by one or two alkyl of 1 to 4 carbon atoms,
R$_5$ is alkyl of 1 to 30 carbon atoms, cycloalkyl of 5 or 12 carbon atoms, phenylalkyl of 7 to 9 carbon atoms, phenyl or said phenylalkyl or said phenyl substituted on the phenyl ring by one or two alkyl of 1 to 4 carbon atoms,
when n is 2-4; E is —CH$_2$CH(R$_3$)COO— where the oxygen atom is attached to T, and
T is an n-valent radical of an alkanepolyol of 3 to 12 carbon atoms after removal of the OH groups.

Preferably, R$_1$ and R$_2$ are independently alkyl of 1 to 12 carbon atoms or phenylalkyl of 7 to 9 carbon atoms.
R$_3$ is preferably hydrogen.
Preferably, R$_4$ is alkyl of 1 to 18 carbon atoms.
Preferably R$_5$ is alkyl of 1 to 18 carbon atoms or phenyl.
Preferably, n is 1-3.
When n is 2, R$_3$ is preferably hydrogen and T is alkylene of 2 to 10 carbon atoms.
When n is 3, R$_3$ is preferably hydrogen and T is alkanetriyl of 3 to 10 carbon atoms.
Most preferably, R$_1$ and R$_2$ are independently alkyl of 1 to 8 carbon atoms, and especially where R$_1$ is methyl and R$_2$ is tert-butyl.
Most preferably, when n is 2, T is alkylene of 2 to 6 carbon atoms, especially hexamethylene.
Most preferably, when n is 3, T is alkanetriyl of 3 to 6 carbon atoms, especially the alkanetriyl derived from trimethylolpropane.

When any of $R_1$ to $R_5$ is alkyl, such alkyl groups are, for example, methyl, ethyl, isopropyl, n-butyl, tert-butyl, tert-amyl, 2-ethylhexyl, lauryl, n-octadecyl, eicosyl and triacontyl; when said radicals are cycloalkyl, they are, for example, cyclopentyl, cyclohexyl, cyclooctyl and cyclododecyl; when said radicals are phenylalkyl, they are for example, benzyl, phenethyl, α-methylbenzyl and α,α-dimethylbenzyl; when said radicals are substituted phenyl, they are, for example, tolyl or xylyl. When T is an n-valent radical derived from an alkanepolyol by removal of the OH groups, it is, for example, ethylene, trimethylene, tetramethylene, 2,2-dimethyl-1,3-propanediyl, hexamethylene, octamethylene, decamethylene, pentaerythrityl, the alkanetriyl radical derived from trimethylolpropane, and $-CH_2CH_2X(CH_2CH_2X)_qCH_2CH_2-$ where q is 0 to 10 and X is $-O-$, $-S-$ or $-NR_1-$.

The compounds of this invention are conveniently prepared by the addition of a mercaptan group of a 2,6-dialkyl-4-mercaptoaniline across an activated ethylenic double bond or of a sulfenyl chloride of a 2,6-dialkyl-4-mercaptoaniline to a trialkyl or triaryl phosphite. The 2,6-dialkyl-4-mercaptoanilines are conveniently prepared by the reduction of the corresponding 4,4'-thiobis(2,6-dialkylanilines) using catalytic hydrogenation or other conventional reducing agents such as zinc dust. The 4,4'-thiobis(2,6-dialkylanilines) are prepared by the methods described in U.S. Pat. Nos. 3,156,720 and 3,224,972 by reaction of a 2,6-dialkylaniline with sulfur dichloride in an inert solvent. The sulfenyl chloride of a 2,6-dialkyl-4-mercaptoaniline is conveniently prepared from the corresponding 4,4'-dithiobis compound in situ by reaction with chlorine as described by N. Kharasch et al, Chem. Rev. 39, 269 (1946). The 2,6-dialkylanilines and the other materials needed to make the instant compounds are largely items of commerce.

Another aspect of the instant invention is a composition stabilized against oxidative or thermal degradation which comprises
  (a) an organic material subject to oxidative or thermal degradation, and
  (b) an effective stabilizing amount of a compound of formula I.

The organic material of this invention is preferably a synthetic polymer, most preferably a polyolefin, especially polypropylene; or an elastomer, e.g. polybutadiene; or is a lubricant, preferably a motor oil, especially a motor oil for a gasoline engine.

Still another aspect of the instant invention is a new intermediate mercaptan of formula VII

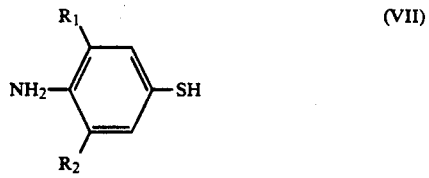

(VII)

wherein
  $R_1$ and $R_2$ are independently alkyl of 1 to 18 carbon atoms, cycloalkyl of 5 to 12 carbon atoms, phenylalkyl of 7 to 9 carbon atoms or said phenylalkyl substituted on the phenyl ring by alkyl of 1 to 4 carbon atoms,
  with the proviso that $R_1$ and $R_2$ are not both ethyl, isopropyl or sec-butyl; that $R_1$ is not methyl when $R_2$ is ethyl or sec-butyl; or that $R_1$ is not isopropyl when $R_2$ is ethyl or tert-butyl.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber; and lubricating oils.

In general polymers which can be stabilized include
1. Polymers of monoolefins and diolefins, for example polyethylene (which optionally can be cross-linked), polypropylene, polyisobutylene, polybutene-1, polymethylpentene-1, polyisoprene or polybutadiene, as well as polymers of cycloolefins, for instance of cyclopenteneor norbornene.
2. Mixtures of the polymers mentioned under 1), for example mixtures of polypropylene with polyisobutylene.
3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.
4. Polystyrene, poly-(p-methylstyrene).
5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.
6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.
7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.
8. Polymers which are derived from α,β-unsaturated acids and derivatives thereof, such as polyacrylates and polymethacrylates, polyacrylamide and polyacrylonitrile.
9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.
10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.
11. Homopolymers and copolymers of cyclic ethers, such as polyalkylene glycols, polyethylene oxide, polypropylene oxide or copolymers thereof with bis-glycidyl ethers.
12. Polyacetals, such as polyoxymethylene and those polyoxymethylenes which contain ethylene oxide as comonomer.
13. Polyphenylene oxides and sulfides, and mixtures of polyphenylene oxides with polystyrene.
14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).
15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.
16. Polyureas, polyimides and polyamide-imides.
17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.
18. Polycarbonates.
19. Polysulfones, polyethersulfones and polyetherketones.
20. Crosslinked polymers which are derived from aldehydes on the one hand and phenols, ureas and melamines on the other hand, such as phenol/formaldehyde resins, urea/formaldehyde resins and melamine/formaldehyde resins.
21. Drying and non-drying alkyd resins.
22. Unsaturated polyester resins which are derived from copolyesters of saturated and unsaturated dicarboxylic acids with polyhydric alcohols and vinyl compounds as crosslinking agents, and also halogen-containing modifications thereof of low flammability.
23. Thermosetting acrylic resins, derived from substituted acrylic esters, such as epoxy-acrylates, urethane-acrylates or polyester acrylates.
24. Alkyd resins, polyester resins or acrylate resins in admixture with melamine resins, urea resins, polyisocyanates or epoxide resins as crosslinking agents.
25. Crosslinked epoxide resins which are derived from polyepoxides, for example from bis-glycidyl ethers or from cycloaliphatic diepoxides.
26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.
27. Mixtures of polymers as mentioned above, for example PP/EPDM, Polyamide 6/EPDM or ABS, PVC/EVA, PVC/ABS, PVC/MBS, PC/ABS, PBTP/ABS.
28. Naturally occuring and synthetic organic materials which are monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratio, which materials may be used as plasticizers for polymers or as textile spinning oils, as well as aqueous emulsions of such materials.
29. Aqueous emulsions of natural or synthetic rubber, e.g. natural latex or latices of carboxylated styrene/butadiene copolymers.
30. Polysiloxanes such as the soft, hydrophilic polysiloxanes described, for example, in U.S. Pat. No. 4,259,467; and the hard polyorganosiloxanes described, for example, in U.S. Pat. No. 4,355,147.
31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
32. Radiation curable compositions containing ethylenically unsaturated monomers or oligomers and a polyunsaturated aliphatic oligomer.
33. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. ANTIOXIDANTS 1.1. Alkylated monophenols, for example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers, for example,
2,2'-thio-bis-(6-tert-butyl-4-methylphenol)
2,2'-thio-bis-(4-octylphenol)
4,4'-thio-bis(6-tert-butyl-3-methylphenol)
4,4'-thio-bis(6-tert-butyl-2-methylphenol)

1.4. Alkylidene-bisphenols, for example,
2,2'-methylene-bis(6-tert-butyl-4-methylphenol)
2,2'-methylene-bis(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl-butane
2,6-di(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl]terephthalate.

1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl)sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl)isocyanurate
1,3,5-tris(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Esters of β-(3,5-tert-butyl-4-hydroxyphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy-3-methylphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-tert-butyl-4-hydroxyphenylpropionyl)-hydrazine 1.10 Diarylamines, for example, diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV ABSORBERS AND LIGHT STABILIZERS 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxyocta-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydoxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ester or isooctyl ester, α-carbomethoxy-cinnamic acid methyl ester, α-cyano-β-methyl-p-methoxycinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-trazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone).

2.7. Oxalic acid diamides, for example, 4,4'-dioctyloxy-oxanilide, 2,2'-di-octyloxy-5,5'-di-tert-butyl-oxanilide, 2,2'-di-dodecyloxy-5,5'-di-tert-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and paramethoxy- as well of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)-phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearylsorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetraayl tetrakis(3,5-di-tert-butyl-4-hydroxyhydrocinnamate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the group consisting of bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)-butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2] heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylene-bis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-2,2,6,6-tetramethyl-piperidin-4-yl)-amino-s-triazin-2-yl]-1,10-diamino-4,7-diazadecane, mixed [2,2,6,6-tetramethylpiperidin-4-yl/$\beta,\beta,\beta',\beta'$-tetramethyl-3,9-(2,4,8,10-tetraoxaspiro[5.5]-undecane) diethyl] 1,2,3,4-butanetetracarboxylate, mixed [1,2,2,6,6-pentamethylpiperidin-4-yl/$\beta,\beta,\beta',\beta'$-tetramethyl-3,9-(2,4,8,10-tetraoxaspiro[5.5]undecane)diethyl] 1,2,3,4-butanetetracarboxylate, 1,2,3,4-butanetetracarboxylate, octamethylene bis(2,2,6,6-tetramethylpiperidin-4-carboxylate) and 4,4'-ethylenebis(2,2,6,6-tetramethylpiperazin-3-one).

A most preferred hindered amine compound is bis(2,2,6,6-tetramethylpiperidin-4-yl) sebacate, the polycondensation product of 1-(2-hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis-(amino-2,2,6,6-tetramethylpiperidine) or N,N',N'',N'''-tetrakis[(4,6-bis(butyl-(2,2,6,6-tetramethyl-piperidin-4-yl)amino)-s-triazine-2-yl]1,10-diamino-4,7-diazadecane.

The following examples are presented for the purpose of illustration only and are not to be construed to limit the nature or scope of the instant invention in any manner whatsoever.

EXAMPLE 1

4-Amino-5-tert-butyl-3-methylbenzenethiol

To a stirred mixture of 5 g of 4,4'-polythiobis(2-tert-butyl-6-methylaniline), 75 g of zinc dust, 10 mL of ethanol and 20 mL of toluene is added dropwise over a three-hour period 40 mL of concentrated hydrochloric acid. The reaction mixture is stirred for 24 hours at room temperature and then the acidic mixture is cautiously neutralized with 5% aqueous sodium hydride. The heterogeneous reaction mixture is extracted with diethyl ether and the extracts are dried over anhydrous sodium sulfate. The solvent is removed in vacuo. To the residue is added 20 mL of heptane and the resultant solid is removed by filtration. The heptane is removed in vacuo and the residue distilled to give 1.3 g of the title compound as a colorless liquid, bp 170° C. (0.3 mm).

Analysis: Calcd. for $C_{11}H_{17}NS$: C, 67.6; H, 8.8; N, 7.2. Found: C, 67.6; H, 9.0; N, 7.3.

EXAMPLE 2

Methyl 3-(4-Amino-3-tert-butyl-5-methylphenylthio)propionate

To a stirred solution of 1.00 g (5.1 mmol) of 2-tert-butyl-4-mercapto-6-methylaniline and 0.05 g (0.5 mmol) of triethylamine in 5 mL of toluene at −5° C. is added dropwise a solution of 0.44 g (5.1 mmol) of methyl acrylate in 5 mL of toluene. The reaction mixture is stirred for 24 hrs at room temperature. The solvent is removed in vacuo and the crude product is purified by flash column chromatography (silica gel, 95:5, heptane:ethyl acetate eluent) to give 0.95 g (66%) of the title compound as a colorless liquid.

$^1$HNMR (CDCl$_3$) (80 MHz) 1.42 (s, 9H), 2.13 (s, 3H), 2.56 (t, 2H), 2.98 (t, 2H), 3.67 (s, 3H), 3.89 (exchangeable s, 2H), 7.12 (meta d, 2H).

Analysis: Calcd. for $C_{15}H_{23}NO_2S$: C, 64.0; H, 8.2; N, 5.0. Found: C, 64.0; H, 8.4; N, 5.1.

EXAMPLE 3

Octadecyl 3-(4-Amino-3-tert-butyl-5-methylphenylthio)propionate

A stirred solution of 4.5 g (23 mmol) of 2-tert-butyl-4-mercapto-6-methylaniline, 7.5 g (23 mmol) of octadecyl acrylate and 0.2 g (2 mmol) of triethylamine in 50 mL of toluene is heated at 50° C. for 18 hrs. The solvent is removed in vacuo and the residue is purified by preparative HPLC (silica gel, 9:1, heptane:ethyl acetate eluent) to give 8.6 g (72%) of the title compound as a colorless liquid.

$^1$HNMR (CDCl$_3$) (90 MHz) 1.31 (t, 3H), 1.24 (s, 32H), 1.42 (s, 9H), 2.13 (s, 3H), 2.53 (t, 2H), 3.00 (t, 2H), 3.80 (exchangeable s, 2H), 4.06 (t, 2H), 7.18 (meta d, 2H).

Analysis: Calcd. for $C_{32}H_{57}NO_2S$: C, 73.9; H, 11.0; N, 2.7. Found: C, 73.7; H, 11.2; N, 2.6.

EXAMPLE 4

N-Octadecyl-2-(4-amino-3-tert-butyl-5-methylphenylthio)succinimide

A stirred solution of 2.8 g (14 mmol) of 2-tert-butyl-4-mercapto-6-methylaniline, 5.0 g (14 mmol) of N-octadecylmaleimide and 0.1 g (1 mmol) of triethylamine in 50 mL of toluene is heated at 50° C. for 18 hours. The solvent is removed in vacuo and the residue is purified by preparative HPLC (silica gel, 4:1, heptane:ethyl acetate eluent) to give 4.3 g (55%) of the title compound as a caramel-colored liquid.

$^1$HNMR (CDCl$_3$3) (90 MHz) 0.84 (t, 3H), 1.20 (s, 32H), 1.35 (s, 9H), 2.08 (s, 3H), 2.62 (dd, 1H), 3.02 (dd, 1H), 3.28 (t, 2H) 3.77 (dd, 1H) 3.95 (exchangeable s, 2H), 7.15 (meta d, 2H).

Analysis: Calcd. for $C_{33}H_{56}N_2O_2S$: C, 72.7; H, 10.4; N, 5.1. Found: C, 72.3; H, 10.5; N, 5.1.

EXAMPLE 5

N-methyl-2-(4-amino-3-tert-butyl-5-methylphenylthio)-succinimide

A stirred solution of 1.0 g (5 mmol) of 2-tert-butyl-4-mercapto-6-methylaniline, 0.6 g (5 mmol) of N-methylmaleimide and 0.1 g (1 mmol) of triethylamine in 10 mL of toluene is heated at 50° C. for 18 hours. The solvent is removed in vacuo and the residue is purified by flash chromatography (silica gel, 3:2, heptane:ethyl acetate eluent) followed by recrystallization from a heptane:toluene solvent mixture to give 0.8 g (51%) of the title compound as a white solid melting at 92°–94° C.

$^1$HNMR (CDCl$_3$) (90 MHz) 1.37 (s, 9H), 2.08 (s, 3H), 2.66 (dd, 1H), 3.06 (dd, 1H), 2.80 (s, 3H) 3.82 (dd, 1H) 4.02 (exchangeable s, 2H), 7.15 (meta d, 2H).

Analysis: Calcd. for C$_{16}$H$_{22}$N$_2$O$_2$S: C, 62.7; H, 7.2; N, 9.1. Found: C, 62.6; H, 7.0; N, 9.0.

EXAMPLE 6

Hexamethylene Bis[3-(4-amino-3-tert-butyl-5-methylphenylthio)propionate

A stirred solution of 4.9 g (25 mmol) of 2-tert-butyl-4-mercapto-6-methylaniline, 2.8 g (12 mmol) of 1,6-hexanediol diacrylate and 0.2 g (2 mmol) of triethylamine in 25 mL of toluene is heated at 50° C. for 18 hours. The solvent is removed in vacuo and the residue is purified by preparative HPLC (silica gel, 3:1, heptane:ethyl acetate eluent) to give 3.4 g (44%) of the title compound as a colorless liquid.

$^1$HNMR (CDCl$_3$) (90 MHz) 1.41 (s, 8H) 1.42 (s, 18H), 2.13 (s, 6H), 2.57 (t, 4H), 3.02 (t, 4H), 3.91 (exchangeable s, 4H), 4.08 (t, 4H), 7.20 (meta d, 4H).

Analysis: Calcd. for C$_{34}$H$_{52}$N$_2$O$_4$S: C, 66.2; H, 8.5; N, 4.5. Found: C, 66.2; H, 8.5; N, 4.4.

EXAMPLE 7

ω-(Acryloyloxy)hexyl 3-(4-Amino-3-tert-butyl-5-methylphenylthio)propionate

The title compound is isolated during the purification of the product of Example 6 in a yield of 1.9 g as a colorless liquid.

$^1$HNMR (CDCl$_3$) (90 MHz) 1.41 (s, 8H), 1.42 (s, 9H), 2.13 (s, 3H), 2.57 (t, 2H), 3.02 (t, 2H), 3.91 (exchangeable s, 2H), 4.08 (complex mult., 4H), 6.13 (complex mult., 3H), 7.20 (meta d, 2H).

Analysis: Calcd. for C$_{23}$H$_{35}$NO$_4$S: C, 65.5; H, 8.4; N, 3.3. Found: C, 65.7; H, 8.1; N, 3.6.

EXAMPLE 8

Di-n-butyl 2-(4-Amino-3-tert-butyl-5-methylphenylthio)succinate

To a stirred solution of 1.00 g (5.1 mmol) of 2-tert-butyl-4-mercapto-6-methylaniline and 0.05 g (0.5 mmol) of triethylamine in 5 mL of toluene at room temperature is added dropwise a solution of 1.16 g (5.1 mmol) of di-n-butyl maleate in 5 mL of toluene. The reaction mixture is stirred for 18 hours at room temperature. The solvent is removed in vacuo and the crude product is purified by flash column chromatography (silica gel, 85:15, heptane:ethylacetate eluent) to give 0.60 g (28%) of the title compound as a colorless liquid.

$^1$HNMR (CDCl$_3$) (80 MHz) 0.91 (t, 6H), 1.42 (s, 17H), 2.13 (s, 3H), 2.64 (dd, 1H), 2.93 (dd, 1H), 3.84 (dd, 1H), 4.08 (t, 4H), 7.20 (meta d, 2H).

Analysis: Calcd. for C$_{23}$H$_{37}$NO$_4$S: C, 65.2; H, 8.8; N, 3.3. Found: C, 64.8; H, 8.7; N, 3.2.

EXAMPLE 9

Methyl 3-(4-Amino-3-tert-butyl-5-methylphenylthio)-2-methylpropionate

To a stirred solution of 1.00 g (5.1 mmol) of 2-tert-butyl-4-mercapto-6-methylaniline and 0.15 g (0.5 mmol) of tetrabutylammonium fluoride in 5 mL of toluene at −5° C. is added dropwise a solution of 0.51 g (5.1 mmol) of methyl methacrylate in 5 mL of toluene. The reaction mixture is stirred for 24 hours at room temperature. The reaction mixture is then poured into 50 mL of water. The phases are separated and the organic phase is dried over anhydrous sodium sulfate. The solvent is removed in vacuo and the residue is purified by flash column chromatography (silica gel, 4:1, heptane:ethyl acetate eluent) to give 0.28 g (18%) of the title compound as a colorless liquid.

$^1$HNMR (CDCl$_3$) (90 MHz) 1.24 (d, 3H), 1.43 (s, 9H), 2.18 (s, 3H), 2.65 (dt, 1H), 2.77 (dd, 1H), 3.11 (dd, 1H) 3.68 (s, 3H), 3.89 (exchangeable s, 2H), 7.18 (meta d, 2H).

Analysis: Calcd. for C$_{16}$H$_{25}$NO$_2$S: C, 65.0; H, 8.5; N, 4.7. Found: C, 65.4; H, 8.6; N, 4.7.

EXAMPLE 10

N-(4-Amino-3-tert-butyl-5-methylphenylthio)methyl-N,N-diphenylamine

To a stirred solution of 4.5 g (23 mmol) of 2-tert-butyl-4-mercapto-6-methylaniline and 3.9 g (23 mmol) of diphenylamine in 30 mL of methanol at −5° C. is added 0.9 g (23 mmol) of formaldehyde as a 37% aqueous solution (1.9 mL). The reaction mixture is stirred for 72 hours at room temperature and then is heated for 5 hours at 50°–55° C. The solvent is removed in vacuo and the residue is purified by flash column chromatography (silica gel, 9:1, heptane:ethyl acetate eluent) to give 3.9 g (45%) of the title compound as a colorless liquid.

$^1$HNMR (CDCl3) (90 MHz) 1.36 (s, 9H), 2.04 (s, 3H), 3.84 (exchangeable s, 2H), 5.11 (s, 2H), 7.06 (complex m, 12H).

Analysis: Calcd. for C$_{24}$H$_{28}$N$_2$S: C, 76.6; H, 7.5; N, 7.4. Found: C, 76.3; H, 7.5; N, 7.3.

EXAMPLE 11

S-(4-Amino-3-tert-butyl-5-methylphenyl)-O,O-di-n-butyl-phosphorothiolate

To a stirred suspension of 15.5 g (40 mmol) of 4,4'-dithiobis(2-tert-butyl-6-methylaniline) in 50 mL of toluene at −40° C. is added 3.4 g (48 mmol) of chlorine gas through a gas inlet tube below the surface of the reaction mixture over a 15–20 minute period. The mixture is stirred for 15 minutes and to it is added 22.0 g (88 mmol) of tributyl phosphite. The reaction mixture is stirred for 24 hours at room temperature and then is filtered to remove insolubles. The solvent is removed in vacuo from the filtrate and the residue is purified by preparative HPLC (silica gel, 7:3, heptane:ethyl acetate) to give 2.7 g (27%) of the title compound as a colorless liquid.

¹HNMR (CDCl₃) (90 MHz) 0.89 (overlapping t, 6H), 1.42 (complex m, 17H), 2.13 (s, 3H), 4.04 (complex m, 4H), 7.20 (meta d, 2H).

Analysis: Calcd. for $C_{19}H_{34}NO_3PS$: C, 58.9; H, 8.8; N, 3.6. Found: C, 58.8; H, 8.9; N, 3.6.

EXAMPLE 12

S-(4-Amino-3-tert-butyl-5-methylphenyl)-O,O-dimethyl-phosphorothiolate

To a stirred suspension of 15.5 g (40 mmol) of 4,4'-dithiobis(2-tert-butyl-6-methylaniline) in 50 mL of toluene at −40° C. is added 3.4 g (48 mmol) of chlorine gas through a gas inlet tube below the surface of the reaction mixture over a 15–20 minute period. The mixture is stirred for 15 minutes and to it is added 10.9 g (88 mmol) of trimethyl phosphite. The reaction mixture is stirred for 24 hours at room temperature and then is filtered to remove insolubles. The solvent is removed in vacuo from the filtrate. The residue is purified by preparative HPLC (silica gel, 1:1, heptane:ethyl acetate) followed by recrystallization from a heptane:toluene solvent mixture to give 2.6 g (27%) of the title compound as a white solid melting at 85°–88° C.

¹HNMR (CDCl3) (90 MHz) 1.42 (s, 9H), 2.13 (s, 3H), 3.82 (d, 6H), 4.00 (s, 2H), 7.20 (meta d, 2H).

Analysis: Calcd. for $C_{13}H_{22}NO_3PS$: C, 51.5; H, 7.3; N, 4.6. Found: C, 51.1; H, 7.3; N, 4.6.

EXAMPLE 13

N-Phenyl-2-(4-amino-3-tert-butyl-5-methylphenylthio)-succinimide

A stirred solution of 1.0 g (5 mmol) of 2-tert-butyl-4-mercapto-6-methylaniline, 0.9 g (5 mmol) of N-phenyl-maleimide and 0.1 g (1 mmol) of triethylamine in 10 mL of toluene is heated at 50° C. for 18 hours. The solvent is removed in vacuo and the residue is purified by flash chromatography (silica gel, ethyl acetate eluent) to give 0.7 g (37%) of the title compound as a white solid melting at 126°–128° C.

¹HNMR (CDCl₃) (90 MHz) 1.40 (s, 9H), 2.13 (s, 3H), 2.93 (dd, 1H), 3.33 (dd, 1H), 2.97 (dd, 1H), 4.06 (exchangeable s, 2H), 7.19 (complex m, 7H).

Analysis: Calcd. for $C_{21}H_{24}N_2O_2S$: C, 68.4; H, 6.6; N, 7.6. Found: C, 68.3; H, 6.4; N, 7.5.

EXAMPLE 14

1,1,1-Tri[5-(4-amino-3-tert-butyl-5-methylphenylthio)-2-oxa-3-oxopentyl)propane

A solution of 2.0 g (10 mmol) of 2-tert-butyl-4-mercapto-6-methylaniline, 1.0 g (3 mmol) of trimethylopropane triacrylate and 0.1 g (1 mmol) of triethylamine in 20 mL of toluene is heated at 50° C. for 18 hours. The solvent is removed in vacuo and the residue is purified by preparative HPLC (silica gel, 7:3, heptane:ethyl acetate eluent) to give 0.6 g (22%) of the title compound as a colorless liquid.

¹H NMR (CDCl3) (90 MHz) 0.88 (t, 3H), 1.46 (s, 27H), 1.46 (q, 2H), 2.13 (s, 9H), 2.57 (t, 6H), 2.97 (t, 6H), 3.91 (exchangeable s, 6H), 4.04 (s, 6H), 7.15 (meta d, 6H).

EXAMPLE 15

2,2-Di(2-oxa-3-oxo-5-(4-amino-3-tert-butyl-5-methylphenylthio)pentyl)butyl acrylate From the residue of Example 14, 0.7 g of the diadduct title compound is isolated as a colorless liquid.

¹HNMR (CDCl₃) (90 MHz) 0.88 (t, 3H), 1.42 (s, 18H), 1.46 (q, 2H), 2.13 (s, 6H), 2.53 (t, 4H), 2.93 (t, 4H), 3.91 (exchangeable s, 4H), 4.04 (s, 4H), 4.08 (s, 2H), 6.10 (complex m, 3H), 7.15 (meta d, 4H).

Analysis: Calcd. for $C_{37}H_{54}N_2O_6S_2$: C, 64.7; H, 7.9; N, 4.1. Found: C, 64.9; H, 8.1; N, 3.9.

EXAMPLE 16

Stabilization of Polypropylene

The base resin formulation comprises unstabilized, new technology polypropylene (PROFAX 6501, HIMONT) containing 0.1% by weight of calcium stearate. The test stabilizer is solvent blended onto the polypropylene from a solution in methylene chloride. After removal of the solvent by evaporation under reduced pressure, the stabilized resin is extruded at 80 rpm from a 1 inch (2.54 cm) extruder at 536° F. (280° C.). The residence time is 45 seconds.

The resin pellets obtained are milled into 25 mil (0.635 mm) thick plaques. The plaques are placed in a forced draft oven at 150° C. and the time in hours till failure is observed. Failure is considered to occur on the showing of the first signs of decomposition such as cracking or brown edges on the plaques.

The results are given in the table below.

| Additive* Compound of | Additive Concentration (% by weight) | Oxidative Stability Time to Failure (hours) |
| --- | --- | --- |
| Base resin** | none | <20 |
| Base resin plus DSTDP (3% by weight) | none | <20 |
| Example 3 | 0.2 | 80 |
| Example 4 | 0.2 | 80 |
| Example 6 | 0.2 | 70 |
| Example 6 plus DSTDP | 0.1 0.3 | 200 |
| Example 10 plus DSTDP | 0.1 0.3 | 70 |

*DSTDP is the thiosynergist distearyl thiodipropionate.
**Base resin contains 0.1% by weight of calcium stearate.

These data show that the instant compounds are effective thermal and oxidative stabilizers for polypropylene, particularly in the presence of the thiosynergist DSTDP.

EXAMPLE 17

Standard Test Method for Oxidation Stability of Gasoline Automotive Engine Oils by Thin-Film Oxygen Uptake (TFOUT)

The antioxidant effectiveness of the instant stabilizers is evaluated by the ASTM test method, D4742. A 1.5 gram test sample of a 10W-30 engine oil, formulated to meet SD/CC quality level containing 0.5% by weight of the test compound is placed in the test apparatus. The test is then completed according to the standard method procedure and the oxidation induction time, in minutes, is reported in the table below. A longer induction time indicates greater oxidation stability.

| Test Compound of Example | Oxidation Induction Time (minutes) |
| --- | --- |
| Base Oil (no stabilizer) | 110 |
| Example 3 | 125 |

EXAMPLE 18

Inhibition of Oxidation of Petroleum Turbine Oil

This test is performed according to ASTM procedure D 943-81.

A 300 ml sample of 150N paraffinic mineral oil (base oil A) containing 0.25% by weight of the compound of Example 3 and 60 ml of distilled water are charged into a large glass tube and heated by an oil bath maintained at 95° C. Oxygen is bubbled at a rate of 3 liters per hour through the delivery tube and through the oil mixture. Iron-copper catalyst coils are mounted in the oxygen delivery tube. Samples of oil are removed periodically and the acid number determined. A low acid number and a low sludge value indicate good stabilization efficacy for the test compound.

| Additive of | Acid Number* | Sludge Value (mg) |
|---|---|---|
| Base Oil | >1 | >1000 |
| Example 3 | 0.41 | 56.7 |

*mg KOH/gram.

What is claimed is:

1. A compound of formula I

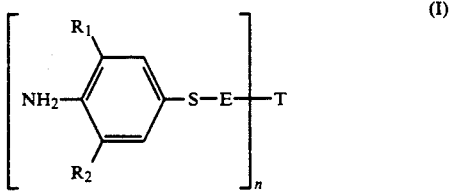

wherein $R_1$ and $R_2$ are independently alkyl of 1 to 18 carbon atoms, cycloalkyl of 5 to 12 carbon atoms, phenylalkyl of 7 to 9 carbon atoms or said phenylalkyl substituted on the phenyl ring by alkyl of 1 to 4 carbon atoms, n is an integer from 1 to 4, when n is 1, E is a direct bond, and T is a group of formula II, III, or IV

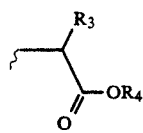 II

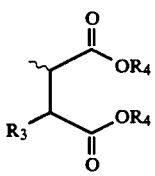 III

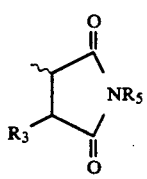 IV where $R_3$ is hydrogen or methyl, $R_4$ is alkyl of 1 to 30 carbon atoms, cycloalkyl of 5 to 12 carbon atoms, phenylalkyl of 7 to 9 carbon atoms, phenyl or said phenylalkyl or said phenyl substituted on the phenyl ring by one or two alkyl of 1 to 4 carbon atoms, $R_5$ is alkyl of 1 to 30 carbon atoms, cycloalkyl of 5 or 12 carbon atoms, phenylalkyl of 7 to 9 carbon atoms, phenyl or said phenylalkyl or said phenyl substituted on the phenyl ring by one or two alkyl of 1 to 4 carbon atoms, when n is 2-4; E is $-CH_2CH(R_3)COO-$ where the oxygen atom is attached to T, and T is an n-valent radical of an alkanepolyol of 3 to 12 carbon atoms after removal of the OH groups.

2. A compound according to claim 1 wherein $R_1$ and $R_2$ are independently alkyl of 1 to 12 carbon atoms or phenylalkyl of 7 to 9 carbon atoms.

3. A compound according to claim 1 wherein $R_3$ is hydrogen.

4. A compound according to claim 1 wherein $R_4$ is alkyl of 1 to 18 carbon atoms.

5. A compound according to claim 1 wherein $R_5$ is alkyl of 1 to 18 carbon atoms or phenyl.

6. A compound according to claim 1 wherein n is 1-3.

7. A compound according to claim 1 wherein, when n is 2, $R_3$ is hydrogen and T is alkylene of 2 to 10 carbon atoms.

8. A compound according to claim 1 wherein, when n is 3, $R_3$ is hydrogen and T is alkanetriyl of 3 to 10 carbon atoms.

9. A compound according to claim 1 wherein $R_1$ and $R_2$ are independently alkyl of 1 to 8 carbon atoms.

10. A compound according to claim 9 wherein $R_1$ is methyl and $R_2$ is tert-butyl.

11. A compound according to claim 1 wherein, when n is 2, T is alkylene of 2 to 6 carbon atoms.

12. A compound according to claim 11 wherein T is hexamethylene.

13. A compound according to claim 1 wherein, when n is 3, T is alkanetriyl of 3 to 6 carbon atoms.

14. A compound according to claim 13 wherein T is the alkanetriyl derived from trimethylopropane.

15. The compound according to claim 1 which is methyl 3-(4-amino-3-tert-butyl-5-methylphenylthio)-propionate;

octadecyl 3-(4-amino-3-tert-butyl-5-methylphenylthio)-propionate;

N-octadecyl-2-(4-amino-3-tert-butyl-5-methylphenylthio)-succinimide;

N-methyl-2-(4-amino-3-tert-butyl-5-methylphenylthio)-succinimide;

hexamethylene bis[3-(4-amino-3-tert-butyl-5-methylphenylthio)-propionate;

ω-(acryloyloxy)hexyl 3-(4-amino-3-tert-butyl-5-methylphenylthio)propionate;

di-n-butyl 2-(4-amino-3-tert-butyl-5-methylphenylthio)-succinate;

methyl 3-(4-amino-3-tert-butyl-5-methylphenylthio)-2-methylpropionate;

N-phenyl-2-(4-amino-3-tert-butyl-5-methylphenylthio)-succinimide;

1,1,1-tri[5-(4-amino-3-tert-butyl-5-methylphenylthio)-2-oxa-3-oxopentyl)propane; or 2,2-di(2-oxa-3-oxo-5-(4-amino-3-tert-butyl-5-methylphenyl-thio)pentyl)butyl acrylate.

* * * * *